United States Patent [19]
Grinninger
[11] 4,154,765
[45] May 15, 1979

[54] METHOD FOR BROMINATING CINNAMALACETOPHENONE

[75] Inventor: Lowell D. Grinninger, Hoffman Estates, Ill.
[73] Assignee: PPG Industries, Inc., Pittsburgh, Pa.

[21] Appl. No.: 594,690
[22] Filed: Jul. 10, 1975
[51] Int. Cl.[2] .............. C07C 49/80
[52] U.S. Cl. .............. 260/592
[58] Field of Search .............. 260/592, 590 R, 590 D

[56] References Cited

U.S. PATENT DOCUMENTS 3,576,771 4/1970 Howell et al. .............. 260/45.7
3,766,136 10/1973 Howell et al. .............. 260/45.7

OTHER PUBLICATIONS

Houser, Modern Synthetic Reactions, 2nd Edn. pp. 422–423 (1972).
Hickenbottom, Reactions of Organic Compounds, pp. 32–33 (1957).

*Primary Examiner*—James O. Thomas, Jr.
*Assistant Examiner*—James H. Reamer
*Attorney, Agent, or Firm*—Edward Whitfield

[57] ABSTRACT

An improved method for brominating cinnamalacetophenone is characterized by the use of a saturated aliphatic hydrocarbon as the reaction medium, recycling of the reaction medium as a mother liquor, and the alternating use of stoichiometric amounts and less-than-stoichiometric amounts of bromine in the preparation of cinnamalacetophenone tetrabromide.

13 Claims, No Drawings

METHOD FOR BROMINATING CINNAMALACETOPHENONE

BACKGROUND OF THE INVENTION

Self-extinguishing properties are imparted to organic polymer compositions normally susceptible to burning by incorporating a brominated arylidine ketone into such compositions, according to the teachings of Howell et al in U.S. Pat. No. 3,766,136. Among the more effective flame retardant additives taught by the Howell et al patent is cinnamalacetophenone tetrabromide.

The method taught in Example VIII of said patent for the preparation of cinnamalacetophenone tetrabromide is commercially unsatisfactory, however, because of poor yields of the crude product and the necessity of purifying said product to remove impurities which impart on undesirable color to the product.

There remains a need, therefore, for an economical method for the bromination of cinnamalacetophenone and it is an object of this invention to provide such a method.

SUMMARY OF THE INVENTION

It has been discovered that the bromination of cinnamalacetophenone suspended in a saturated linear aliphatic or cycloaliphatic liquid hydrocarbon proceeds in a surprisingly satisfactory manner to produce the tetrabromide along with small amounts of the dibromide and hexabromide. The color of the product, as isolated from the reaction mixture, ranges from white to a pale greenish-yellow, thus allowing the use of the product in white plastic compositions without further purification. Yields as high as about 92% of theory are obtained and the average yield is about 80%.

DETAILED DESCRIPTION OF THE INVENTION

The saturated linear aliphatic hydrocarbons used as the reaction medium are straight-chained and may have from about 6 to about 12 carbon atoms. Preferably, however, the number of carbon atoms will be from about 6 to about 8. Hexane and heptane are especially preferred among the linear hydrocarbons so defined.

The saturated cycloaliphatic hydrocarbons are the preferred reaction media and may have from about 5 to about 8 carbon atoms. Cyclohexane is especially preferred. A charge of this hydrocarbon may be used repeatedly without rectification in the batch-wise bromination of cinnamalacetophenone. Moreover, such an advantage may be utilized in a continuous operation of the method of this invention.

It will be readily apparent to those skilled in the art that mixtures of the above-designated hydrocarbons may be used.

The temperature at which the bromination reaction is carried out in the hydrocarbon medium may range from about 0° C. to about 80° C. but the preferred range is from about 20° C. to about 60° C. When cyclohexane is used as the reaction medium the preferred temperature is from about 20° C. to about 30° C.

The relative amounts of reaction medium and cinnamalacetophenone may be adjusted to facilitate mixing of the slurries encountered but a weight ratio of hydrocarbon to the reactant within the range of about 5:1 to about 20:1 is usually satisfactory.

A further discovery has been made in connection with the recycling of a cyclohexane reaction medium as a mother liquor in the preparation of subsequent batches of the brominated product, namely, that from about 98% to about 99.5%, by weight, of the stoichiometric amount of bromine (that amount which combines with cinnamalacetophenone to form cinnamalacetophenone tetrabromide) may be used in alternating batches to give excellent and reproducible yields of product having a high melting point and, in particular, good color. Thus, a stoichiometric amount of bromine may be used in the odd-numbered batches of a series while the reduced amount is employed in the even-numbered batches. The purpose of the reduced amounts of bromine is to compensate for the unreacted bromine which may remain in the mother liquor from a preceding batch and thus it will be understood that a strict adherence to the alternating routine is not always necessary. Observation of the mother liquor may indicate that the bromine content is such that the routine should be interrupted until the optimal conditions are re-established. The alternating routine is preferred, however, because of its simplicity and consistency in affording good results.

The time allotted for the physical step of introducing the bromine into a suspension of cinnamalacetophenone in the hydrocarbon is not particularly critical but it is usually complete in about 0.5 hour. Likewise, the holding time after all of the bromine has been introduced is not critical; it may be governed by the color of the reaction mixture but a period of from 45 minutes to one hour is usually sufficient.

The invention is further illustrated by the following examples wherein parts by weight are used unless otherwise indicated.

EXAMPLE 1

Cinnamalacetophenone (35.1 parts, 0.15 mole) is added to about 200 parts of heptane and the resulting slurry is stirred while being heated to about 55° C. before the introduction of 48 parts (0.3 mole) of bromine is commenced. The exotherm of the bromination reaction raises the temperature to about 60° C. during the 23 minute introduction period. The mixture is stirred at 50°-60° C. for about 80 minutes and then it is cooled and filtered. The filter cake and reaction vessel are washed with about 70 parts of heptane. After drying, 63.1 parts (76% of theory) of a satisfactory product are recovered. The pale greenish-yellow product melts at 161.5°-167.5° C.

EXAMPLE 2

Cinnamalacetophenone (35.1 parts, 0.15 mole) is slurried with about 230 parts of cyclohexane at 55° C. while the introduction of 48 parts (0.3 mole) of bromine is started. A temperature of from about 50° C. to about 60° C. is maintained by the exotherm of the bromination. After about one-half of the bromine is in, the reaction mixture becomes a clear solution but precipitation occurs shortly thereafter. The introduction of bromine is completed in a total time of about 40 minutes. A thick slurry of fine particles is obtained but stirring is continued for about one hour. The slurry is cooled and filtered, and the filter cake is washed once with about 100 parts of cyclohexane. The filter cake is dried to give 57.5 parts (69% of theory) of a satisfactory product which melts at 159.5°-165.5° C. Infra-red analysis indicates that about 88% of the product is the tetrabromide and the remainder is made up of approximately equal parts of the dibromide and hexabromide. Elemental analysis of the product shows that it contains 57.27% bromine whereas the theoretical value for the tetrabromide is 57.7%.

EXAMPLES 3 - 6

A series of batches of brominated cinnamalacetophenone is prepared according to the general procedure of Example 2 except that the temperature is maintained within the range of 20° C. to 30° C. throughout the reaction, the reaction medium (550 parts of cyclohexane in Example 3) is recycled as a mother liquor after adjustment for losses, and the weight of bromine in Examples 4 and 6 is 1% less than the stoichiometric amount (48 parts) used in Examples 3 and 5. The yields, colors, and melting points of the products are given in Table 1.

TABLE I

| Example No. | Yield (%) | Color | M.P. (°C.) |
|---|---|---|---|
| 3 | 65.8 | slightly off-white | 167–169 |
| 4 | 81.7 | faintly greenish-white | 155–165 |
| 5 | 82.0 | faintly yellowish-white | 162–168 |
| 6 | 85.4 | faintly yellowish-white | 162–168 |
| Average | 78.7 | | |

EXAMPLE 7

A slurry of 35.1 parts (0.15 mole) of cinnamalacetophenone in about 550 parts of cyclohexane is stirred while the introduction of 48 parts (0.3 mole) of bromine is commenced. The temperature of the reaction mixture is maintained between 20° C. and 30° C. for 0.5 hour while the bromine is introduced. When about half of the bromine is in, the reaction mixture becomes a clear red solution; the solution is seeded with 0.25 part of cinnamalacetophenone tetrabromide and the remainder of the bromine is charged into the reaction vessel. Precipitation begins shortly thereafter and the slurry is stirred for about 30 minutes before it is filtered. The vessel and filter cake are washed twice with 40 part portions of cyclohexane. After drying, 48.6 parts (58.4% of theory) of yellowish-white crystals melting at 163°–168° C. are obtained.

EXAMPLES 8 - 16

The general procedure of Example 7 is repeated in a series of preparations but the mother liquor of each preceding batch is used as the reaction medium in the succeeding batch instead of "virgin" cyclohexane, e.g., the mother liquor from Example 7 is the reaction medium in Example 8. The yields and melting points of the products are listed in Table II.

TABLE II

| Example No. | Yield (%) | M.P. (°C.) |
|---|---|---|
| 8* | 71.9 | 155.5–158.5 |
| 9* | 76.6 | 160–164 |
| 10* | 79.7 | 153–161 |
| 11* | 91.6 | 148.5–153.5 |
| 12 | 90.5 | 150–155 |
| 13* | 102.0** | 146.5–156.5 |
| 14* | 79.8 | 154–158 |
| 15* | 74.4 | 144–152 |
| 16* | 91.8 | 148.5–159.5 |

*$Br_2$ used is 99% of stoichiometric amount of $Br_2$ required for tetrabromide.
**The apparently anomalous yield is caused by precipitation of an extraordinary amount of di- and hexabromides when the mother liquor becomes super-saturated with solute.

The yields of brominated cinnamalacetophenone from Examples 7 through 16 average 81.7% and a blend of the products melts at 151°–158° C.

The Limiting Oxygen Index (ASTM D2863-70) of a polystyrene composition containing the product of the process of this invention is 30.0 whereas a composition containing an equal amount of cinnamalacetophenone tetrabromide in place of the product prepared by the instant process has an L.O.I. of 29.5.

The embodiments of the invention illustrated and described herein are merely illustrative and variations which may differ in detail but not in substance will readily suggest themselves to those skilled in the art. The scope of the invention is not intended to be defined by the illustrative embodiments but the subject matter which the applicant regards as his invention is particularly set forth in the following claims.

I claim:

1. In the method for brominating cinnamalacetophenone which comprises mixing bromine with cinnamalacetophenone in a reaction medium, an improvement consisting essentially of using at least one saturated aliphatic hydrocarbon selected from the group consisting of linear hydrocarbons having from about 6 to about 12 carbon atoms and cycloaliphatic hydrocarbons having from about 5 to about 8 carbon atoms as the reaction medium.

2. The improved method of claim 1 wherein the bromine and cinnamalacetophenone are mixed at a temperature of from about 0° C. to about 80° C.

3. The improved method of claim 2 wherein the temperature is from about 20° C. to about 60° C.

4. The improved method of claim 1 wherein the reaction medium is a saturated cycloaliphatic hydrocarbon having from about 5 to about 8 carbon atoms.

5. The improved method of claim 4 wherein the temperature is from about 0° C. to about 80° C.

6. The improved method of claim 4 wherein the saturated cycloaliphatic hydrocarbon is cyclohexane.

7. The improved method of claim 6 wherein the temperature is from about 20° C. to about 30° C.

8. The improved method of claim 6 characterized further in that the method is practiced in a batch-wise manner and the cyclohexane reaction medium from a first batch is recycled to a subsequent batch as a mother liquor.

9. The improved method of claim 8 characterized further in that an amount of bromine which is stoichiometric in the preparation of cinnamalacetophenone tetrabromide is introduced into said first batch and from about 98% to about 99.5%, by weight, of said stoichiometric amount is introduced into a subsequent batch.

10. The improved method of claim 9 wherein the stoichiometric amount of bromine is introduced into odd-numbered batches of a series and the less-than-stoichiometric amount of bromine is introduced into even-numbered batches.

11. An improved method for preparing cinnamalacetophenone tetrabromide which comprises mixing from about 98% to about 100%, by weight, of the stoichiometric amount of bromine with cinnamalacetophenone in the presence of at least one saturated aliphatic hydrocarbon selected from the group consisting of linear hydrocarbons having from about 6 to about 12 carbon atoms and cycloaliphatic hydrocarbons having from about 5 to about 8 carbon atoms.

12. The improved method of claim 11 characterized further in that the reaction medium is cyclohexane, the temperature is from about 20° C. to about 30° C., and the reaction medium is recycled as a mother liquor from a first batch in a series of batches of the tetrabromide to a subsequent batch.

13. The improved method of claim 12 characterized further in that a stoichiometric amount of bromine is introduced into the odd-numbered batches and from about 98% to about 99.5%, by weight, of said stoichiometric amount is introduced into the even-numbered batches.

* * * * *